United States Patent
Reddy et al.

(10) Patent No.: US 9,233,911 B2
(45) Date of Patent: Jan. 12, 2016

(54) CU-MEDIATED ANNULATION FOR THE PRODUCTION OF 1-AMINO-2-NAPHTHALENECARBOXYLIC ACID DERIVATIVES

(71) Applicant: Council of Scientific & Industrial Research, New Delhi (IN)

(72) Inventors: Santhosh Rekula Reddy, Pune (IN); Kishore Prasad Pragati, Pune (IN); Brij Bhushan Ahuja, Pune (IN); Arumugam Sudalai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/371,059

(22) PCT Filed: Jan. 10, 2013

(86) PCT No.: PCT/IN2013/000019
§ 371 (c)(1),
(2) Date: Jul. 8, 2014

(87) PCT Pub. No.: WO2013/105117
PCT Pub. Date: Jul. 18, 2013

(65) Prior Publication Data
US 2015/0011781 A1   Jan. 8, 2015

(30) Foreign Application Priority Data

Jan. 10, 2012 (IN) .............................. 83/DEL/2012

(51) Int. Cl.
*C07C 227/12* (2006.01)
*C07C 229/68* (2006.01)
*C07C 229/70* (2006.01)
*C07C 229/74* (2006.01)
*C07D 317/70* (2006.01)

(52) U.S. Cl.
CPC ............. *C07C 227/12* (2013.01); *C07C 229/68* (2013.01); *C07C 229/70* (2013.01); *C07C 229/74* (2013.01); *C07D 317/70* (2013.01); *C07C 2103/26* (2013.01)

(58) Field of Classification Search
CPC ........................... C07C 229/74; C07C 227/12
USPC ......................................................... 549/433
See application file for complete search history.

(56) References Cited

FOREIGN PATENT DOCUMENTS

WO    WO2010059773 A1    5/2010

OTHER PUBLICATIONS

Bruncko et al., "Naphthamidine urokinase plasminogen activator inhibitors with improved pharmacokinetic properties", Bioorg Med Chem Lett (2005), 15(1):93-98.
Kobayashi et al., "Efficient Synthesis of 1-Amino-2-naphthalenecarboxylic Acid Derivatives via a Sequential Michael Addition/Enolate-Nitrile Coupling Route and Its Application to Facile Preparation of 9-Amino Analogues of Arylnaphthofuranone Lignans", J Org Chem (1997), 62(3):664-668.

*Primary Examiner* — Taofiq A Solola
(74) *Attorney, Agent, or Firm* — Bret E. Field; Bozicevic, Field & Francis LLP

(57) ABSTRACT

Invention provides a cheaper and practical protocol for the construction of a wide variety of 1-Amino-2-naphthalene-carboxylic acid derivatives and their structural analogues that proceeds with high yields in a single step via intramolecular cascade cyano ene reaction.

6 Claims, No Drawings

CU-MEDIATED ANNULATION FOR THE PRODUCTION OF 1-AMINO-2-NAPHTHALENECARBOXYLIC ACID DERIVATIVES

The following specification particularly describes and ascertains the nature of this invention and the manner in which it is to be performed.

TECHNICAL FIELD OF THE INVENTION

This invention relates to cheaper and practical protocol for the construction of a wide variety of 1-Amino-2-naphthalenecarboxylic acid derivatives and their structural analogues that proceeds with high yields in a single step via intramolecular cascade cyano ene reaction.

1) Rosenmund-von Braun Reaction:

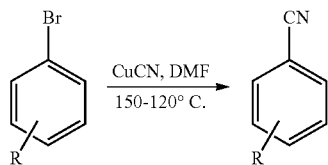

2) Kobayashi et al:

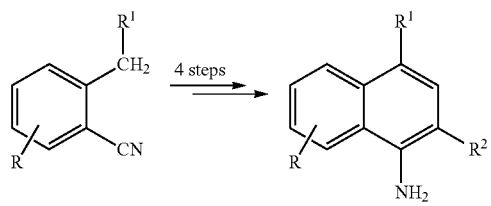

3) This Work:

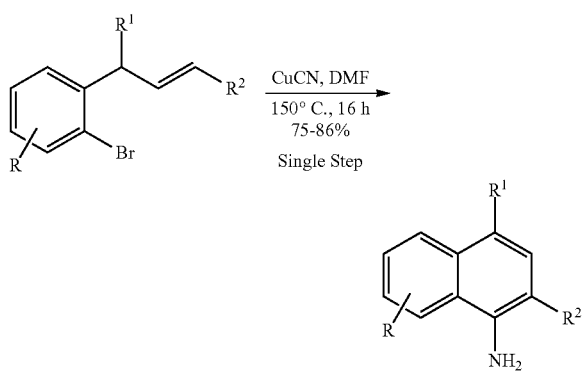

R = alkyl, alkoxy, halo, NO$_2$, CN, etc.
R$^1$ = H, alkyl, aryl
R$^2$ = CO$_2$Et, CO$_2$Me, CO$_2^t$Bu, CN, COCH$_3$, SO$_2$Ph

BACKGROUND AND PRIOR ART OF THE INVENTION

1-Amino-2-naphthalenecarboxylic Acid Derivatives are the intermediates of Dyes and Pigments useful in Peptide Synthesis. There is less literature available on preparation of 1-Amino-2-naphthalenecarboxylic Acid Derivatives. An article titled "Efficient Synthesis of 1-Amino-2-naphthalenecarboxylic Acid Derivatives via a Sequential Michael Addition/Enolate-Nitrile Coupling Route and Its Application to Facile Preparation of 9-Amino Analogues of Arylnaphthofuranone Lignans" by Kazuhiro Kobayashi et al, published in J. Org. Chem 1997, 62, 664-668, wherein, a method for the general preparation of 1-amino-2-naphthalenecarboxylates and nitrites, which is based on the tandem Michael addition/enotate-nitrile coupling reaction between alpha-lithio derivatives of 2-atkylbenzonitriles and alpha-beta unsaturated carboxylic acid derivatives is described.

The reaction of 2-(alpha-lithioalkyl)benzonitriles, generated in situ by treatment of 2-alkylbenzonitriles with LDA in diglyme, with alpha-beta unsaturated carboxylates and nitrites produced 1-amino-3,4-dihydro-2-naphthalenecarboxylates and carbonitriles in 54-98% yields through Michael addition of the lithio nitrites to alpha-beta unsaturated carboxylic acid derivatives, followed by zinc iodide-promoted intra molecular enolate-nitrile coupling of the resulting enolate intermediates. The dihydronaphthalenecarboxylic acid derivatives were converted to the corresponding 1-amino-2-naphthalenecarboxylic acid derivatives in 43-99% yields on dehydrogenation with palladium on activated carbon in refluxing p-cymene. The synthesis is depicted in scheme 1 below.

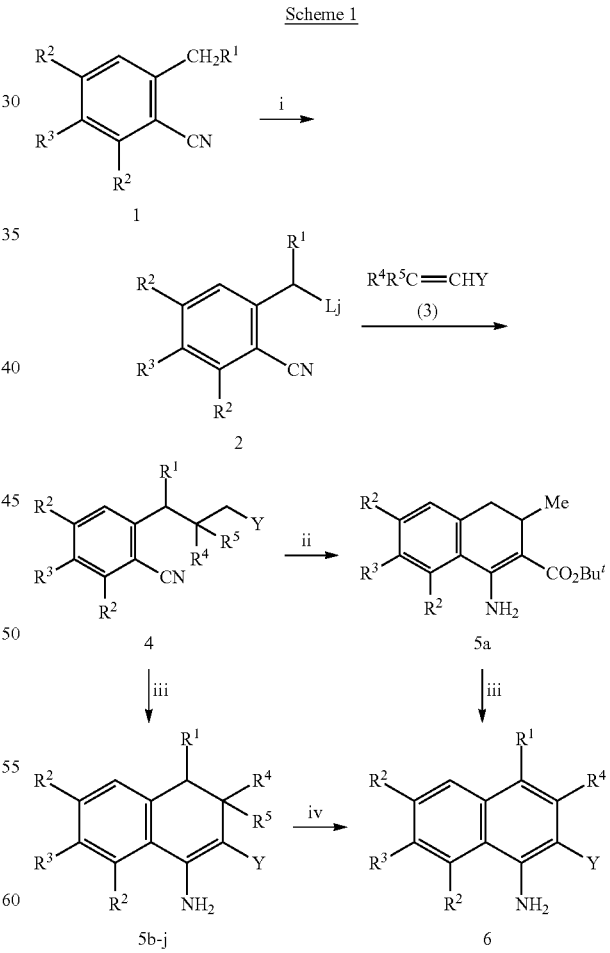

Scheme 1

Reagents and conditions. i. 2LDA, THF, -78° C.; ii. -78° C. to r.t.: iii, ZnI$_2$, -78° C. to r.t.; iv, 10% Pd/C, p-cycmene, reflux The process disclosed in the above prior art involves multiple steps and hence not feasible on industrial scale. Also, the process requires consumption of large quantities of hazardous chemicals with longer reaction time with less efficiency and narrow substrate scope.

OBJECTS OF THE INVENTION

Main object of the present invention is to provide an effective synthesis for the preparation of 1-Amino-2-naphthalenecarboxylic acid and its derivatives with quantitative yields.

SUMMARY OF THE INVENTION

Accordingly, present invention provides a one pot process for the preparation of compound of formula (A) and their structural analogues comprising reacting compound of formula (B) with CuCN in solvent at a temperature in the range of 145°-155° C. for time period in the range of 10 to 12 hours;

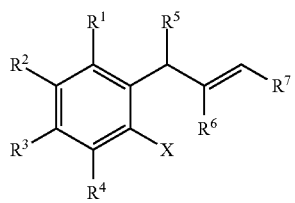

Formula (B)

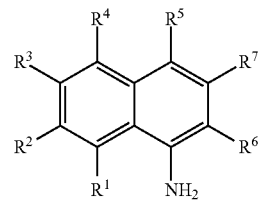

Formula (A)

Wherein, $R^1$, $R^2$, $R^3$, $R^4$ are selected independently from the group consisting of hydrogen, alkyl, alkoxy, halo, $NO_2$ or CN;

$R^5$ is selected independently from the group consisting of H, $CH_3$, $C_2H_5$, Ph or $CH_3C_6H_4$;

$R^6$ is selected independently from the group consisting of $CO_2Et$, $CO_2Me$, $CO_2Ph$, COMe, COPh, CN, $SO_2Ph$, $CONH_2$ or $NO_2$;

$R^7$ is selected independently from the group consisting of H, $CH_3$ of Ph; and X represents halo group.

In an embodiment of the present invention, the polar aprotic solvent is preferably DMF.

In yet another embodiment of the present invention, the halo group is preferably bromo.

In yet another embodiment of the present invention, representative compound of formula (A) comprising:
Ethyl 1-aminonaphthalene-2-carboxylate;
Ethyl 1-amino-6-methoxynaphthalene-2-carboxylate;
Ethyl 1-amino-6,7-dimethoxynaphthalene-2-carboxylate;
Ethyl 1-amino-7,8-dimethoxynaphthalene-2-carboxylate;
Ethyl 1-amino-6-(benzyloxy)-7-methoxynaphthalene-2-carboxylate;
Ethyl 1-amino-6-methylnaphthalene-2-carboxylate;
Ethyl 1-amino-6-fluoronaphthalene-2-carboxylate;
Ethyl 1-amino-6-nitronaphthalene-2-carboxylate;
Ethyl 5-aminonaphtho[2,3-d][1,3]dioxole-6-carboxylate;
Ethyl 1-amino-6,7-dimethoxy-5-methylnaphthalene-2-carboxylate and;
Ethyl 1-aminophenanthrene-2-carboxylate.

In yet another embodiment of the present invention, compound of formula (B) is selected from the group consisting of ethyl 4-(2-halo-4,5-dimethoxyphenyl)but-2-enoate, 1-(2-bromo-4,5-dimethoxyphenyl)but-2-ene derivatives, 1-(2-bromo-3,4,5,6-substituted phenyl)but-2-ene compounds.

In yet another embodiment of the present invention, the preparation of substituted naphthalene amino esters of formula (A) and their structural analogues comprising subjecting the 4-(2-halophenyl)-2-butenoates of formula (B) to intramolecular cascade cyano ene reaction in the presence of CuCN in DMF under reflux condition.

In an embodiment, present invention provides a compound of formula (A)

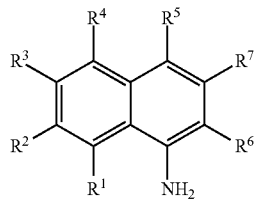

Wherein, $R^1$, $R^2$, $R^3$, $R^4$ are selected independently from hydrogen, alkyl, alkoxy, halo, $NO_2$, CN;

$R^5$ is selected independently from H, $CH_3$, $C_2H_5$, Ph, $CH_3C_6H_4$;

$R^6$ is selected independently from $CO_2Et$, $CO_2Me$, $CO_2Ph$, COMe, COPh, CN, $SO_2Ph$, $CONH_2$, $NO_2$ and $R^7$ is selected independently from H, $CH_3$, Ph.

In yet another embodiment of the present invention, representative compounds of formula A comprising:
i. Ethyl 1-aminonaphthalene-2-carboxylate;
ii. Ethyl 1-amino-6-methoxynaphthalene-2-carboxylate;
iii. Ethyl 1-amino-6,7-dimethoxynaphthalene-2-carboxylate;
iv. Ethyl 1-amino-7,8-dimethoxynaphthalene-2-carboxylate;
v. Ethyl 1-amino-6-(benzyloxy)-7-methoxynaphthalene-2-carboxylate;
vi. Ethyl 1-amino-6-methylnaphthalene-2-carboxylate;
vii. Ethyl 1-amino-6-fluoronaphthalene-2-carboxylate;
viii. Ethyl 1-amino-6-nitronaphthalene-2-carboxylate;
ix. Ethyl 5-aminonaphtho[2,3-d][1,3]dioxole-6-carboxylate;
x. Ethyl 1-amino-6,7-dimethoxy-5-methylnaphthalene-2-carboxylate;
xi. Ethyl 1-aminophenanthrene-2-carboxylate.

DETAILED DESCRIPTION OF THE INVENTION

Present invention provides a facile, cost-effective method involving one-pot CuCN-mediated cyano ene reaction of the compound of formula (B) for the construction of a wide variety of 1-Amino-2-naphthalenecarboxylic acid derivatives of formula (A) and their structural analogues that proceeds with high yields in a single step via intramolecular cascade cyano ene reaction.

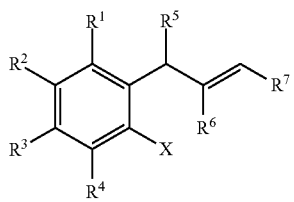

Formula (B)

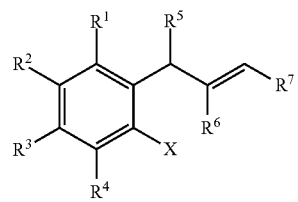

Formula (B)

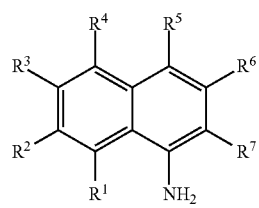

Formula (A)

where, $R^1$ to $R^7$ and X is described herein below.

CuCN is very cheap, easy to perform at higher scales, showed remarkably broad substrate scope and good functional group tolerance and not much effluent is generated.

The one-pot CuCN-mediated cyano ene reaction typically requires substantially similar conditions of Rosenmund-von Braun Reaction. This novel transformation involves cascade reaction sequence, first substitution of bromo with CN and followed by an intramolecular cyano ene reaction to access 1-Amino-2-naphthalenecarboxylic acid derivatives with quantitative yields. The procedure tolerates a series of functional groups, such as methoxyl, fluoro and chloro groups. Otherwise synthesis of 1-Amino-2-naphthalenecarboxylic acid derivatives requires multiple steps.

In an aspect of the invention, 1-Amino-2-naphthalenecarboxylic acid derivatives of formula (A) is represented as enlisted herein.

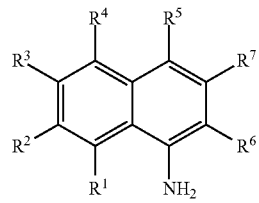

Wherein $R^1$, $R^2$, $R^3$, $R^4$ are selected independently from the group consisting of hydrogen, alkyl, alkoxy, halo, $NO_2$ or CN;

$R^5$ is selected independently from the group consisting of H, $CH_3$, $C_2H_5$, Ph or $CH_3C_6H_4$;

$R^6$ is selected independently from the group consisting of $CO_2Et$, $CO_2Me$, $CO_2Ph$, COMe, COPh, CN, $SO_2Ph$, $CONH_2$ or $NO_2$;

$R^7$ is selected independently from the group consisting of H, $CH_3$ of Ph; and X represents halo group.

Present invention provides a one pot synthesis of various 1-Amino-2-naphthalenecarboxylic acid derivatives of formula (A) and their structural analogues which includes reacting a compound of formula (B) with CuCN in polar aprotic solvent and refluxing the mixture at a temperature in the range of 145-155° C. for 10-12 hours. The compound of formula (B) is wherein $R^1$, $R^2$, $R^3$, $R^4$ are selected independently from the group consisting of hydrogen, alkyl, alkoxy, halo, $NO_2$ or CN;

$R^5$ is selected independently from the group consisting of H, $CH_3$, $C_2H_5$, Ph or $CH_3C_6H_4$;

$R^6$ is selected independently from the group consisting of $CO_2Et$, $CO_2Me$, $CO_2Ph$, COMe, COPh, CN, $SO_2Ph$, $CONH_2$ or $NO_2$;

$R^7$ is selected independently from the group consisting of H, $CH_3$ of Ph; and X represents halo group.

The proposed mechanism is depicted in scheme 2 below:

Scheme 2

The process steps involve tandem reaction sequence where in the first step substitution of bromo with CN and followed by an intramolecular cyano ene reaction to access 1-Amino-2-naphthalenecarboxylic acid derivatives with quantitative yields. The halo group is preferably bromo. The polar aprotic solvent is selected preferably DMF.

In another embodiment, 1-(2-bromo-4,5-dimethoxyphenyl)but-2-ene derivatives are subjected to one-pot CuCN-mediated cyano ene reaction to obtain corresponding 6,7-dimethoxy-1-aminonaphthalene-3-substituted compounds in good yield. The reaction of the present invention may be carried out at 120 to 160° C. in DMF for a period of 10 to 20 hrs to achieve the product in good yields in the range of 75 to 90%. The products may be isolated using column chromatography and further may be purified by crystallization techniques known in the art.

The synthesis of 6,7-dimethoxy-1-aminonaphthalene-3-substituted compounds starting from 1-(2-bromo-4,5-dimethoxyphenyl)but-2-ene derivatives are depicted below in table 1.

TABLE 1

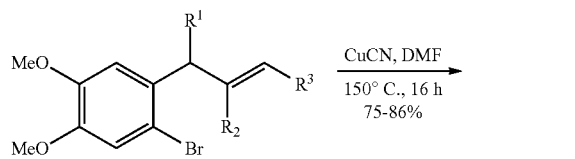

| Entry | $R^1$ | $R^2$ | $R^3$ | Yield (%)[a] |
|---|---|---|---|---|
| 1 | H | $CO_2Et$ | H | 86 |
| 2 | H | $CO_2Me$ | H | 86 |
| 3 | H | $CO_2Ph$ | H | 78 |
| 4 | H | COMe | H | 76 |
| 5 | H | COPh | H | 78 |
| 6 | H | $SO_2Ph$ | H | 75 |
| 7 | H | $NO_2$ | H | 76 |
| 8 | H | $CONH_2$ | H | 82 |
| 9 | Ph | $CO_2Et$ | H | 79 |
| 10 | $CH_3$ | $CO_2Et$ | H | 75 |
| 11 | $C_2H_5$ | $CO_2Et$ | H | 78 |
| 12 | $CH_3C_6H_4$ | $CO_2Et$ | H | 78 |
| 13 | H | $CO_2Et$ | $CH_3$ | 82 |
| 14 | H | $CO_2Et$ | Ph | 78 |
| 15 | H | CN | Ph | 82 |
| 16 | H | $NO_2$ | $CH_3$ | 80 |

[a]Isolated yield after column chromatographic purification.

1-(2-bromo-3,4,5,6-substituted phenyl)but-2-ene compounds are subjected to one-pot CuCN-mediated cyano ene reaction to obtain 5,6,7,8-substituted ethyl 1-aminonaphthalene-2-carboxylate compounds in good yield. The reaction of the present invention can be carried out at 120 to 160° C. in DMF for a period of 10 to 20 hrs to achieve the product in good yields in the range of 75 to 90%. The products may be isolated using column chromatography and further may be purified by crystallization techniques known in the art.

The synthesis of 5,6,7,8-substituted ethyl 1-aminonaphthalene-2-carboxylate compounds starting from 1-(2-bromo-3,4,5,6-substituted phenyl)but-2-ene compounds are depicted below in table 2.

TABLE 2

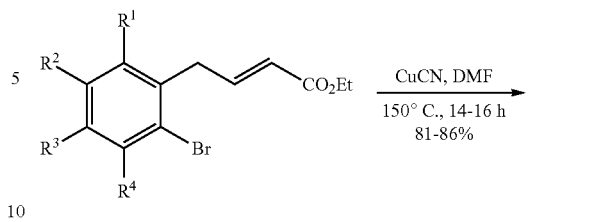

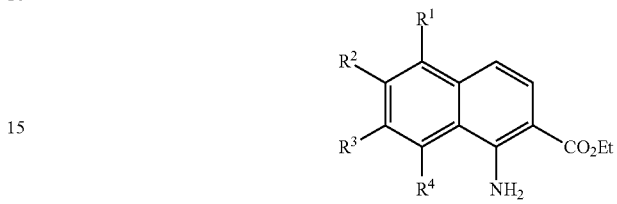

| S. No | $R^1$ | $R^2$ | $R^3$ | $R^4$ | Yield (%)[a] |
|---|---|---|---|---|---|
| 1 | H | H | H | H | 86 |
| 2 | H | OMe | H | H | 86 |
| 3 | H | OMe | OMe | H | 85 |
| 4 | H | H | OMe | OMe | 83 |
| 5 | H | OMe | OMe | OMe | 83 |
| 6 | H | OMe | OMe | OMe | 84 |
| 7 | H | OTs | OMe | H | 83 |
| 8 | H | OBn | OMe | H | 83 |
| 9 | H | H | H | F | 82 |
| 10 | H | $NO_2$ | H | H | 82 |
| 11 | H | CN | H | H | 81 |
| 12 | OMe | OMe | H | H | 83 |
| 13 | H | Me | Me | H | 83 |
| 14 | H | Me | H | H | 82 |
| 15 | H | Cl | H | H | 81 |
| 16 | H | H | H | OMe | 82 |
| 17 | H | —O—$CH_2$—O— | | H | 85 |
| 18 | (E)-ethyl 3-(1-cyanonaphthalen-2-yl)acrylate | | | | 84 |
| 19 | 3-(1-hydroxybut-3-enyl)pyridine-2-carbonitrile | | | | 81 |
| 20 | 1-(3-bromofuran-2-yl)but-3-en-1-ol | | | | 81 |

[a]Isolated yield after column chromatographic purification.

In another preferred embodiment, the present invention discloses compound of formula A

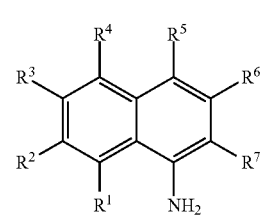

Formula A

Wherein,
$R^1$, $R^2$, $R^3$, $R^4$ are selected independently from hydrogen, alkyl, alkoxy, halo, $NO_2$, CN;
$R^5$ is selected independently from H, $CH_3$, $C_2H_5$, Ph, $CH_3C_6H_4$;
$R^6$ is selected independently from $CO_2Et$, $CO_2Me$, $CO_2Ph$, COMe, COPh, CN, $SO_2Ph$, $CONH_2$, $NO_2$ and
$R^7$ is selected independently from H, $CH_3$, Ph.

1-Amino-2-naphthalenecarboxylic acid derivatives of formula (A) according to the invention encompasses Ethyl 1-aminonaphthalene-2-carboxylate, Ethyl 1-amino-6-methoxynaphthalene-2-carboxylate, Ethyl 1-amino-6,7-dimethoxynaphthalene-2-carboxylate, Ethyl 1-amino-7,8-dimethoxynaphthalene-2-carboxylate, Ethyl 1-amino-6-(benzyloxy)-7-methoxynaphthalene-2-carboxylate, Ethyl 1-amino-6-methylnaphthalene-2-carboxylate, Ethyl 1-amino-6-fluoronaphthalene-2-carboxylate, Ethyl 1-amino-6-nitronaphthalene-2-carboxylate, Ethyl 5-aminonaphtho[2,3-d][1,3]dioxole-6-carboxylate, Ethyl 1-amino-6,7-dimethoxy-5-methylnaphthalene-2-carboxylate, Ethyl 1-aminophenanthrene-2-carboxylate.

Present invention discloses compound of formula B

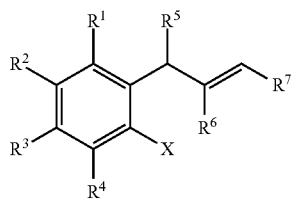

Formula B wherein $R^1$, $R^2$, $R^3$, $R^4$ are selected independently from hydrogen, alkyl, alkoxy, halo, $NO_2$, CN;

$R^5$ is selected independently from H, $CH_3$, $C_2H_5$, Ph, $CH_3C_6H_4$;

$R^6$ is selected independently from $CO_2Et$, $CO_2Me$, $CO_2Ph$, COMe, COPh, CN, $SO_2Ph$, $CONH_2$, $NO_2$;

$R^7$ is selected independently from H, $CH_3$, Ph; and

X represents halo group.

The compound of formula (B) according to the invention, is selected from the group consisting of ethyl 4-(2-halo-4,5-dimethoxyphenyl)but-2-enoate, 1-(2-bromo-4,5-dimethoxyphenyl)but-2-ene derivatives, 1-(2-bromo-3,4,5,6-substituted phenyl)but-2-ene compounds.

EXAMPLES

The following examples are given by way of illustration and therefore should not be construed to limit the scope of the present invention.

Example 1

Typical Procedure for Preparation of 1-Amino-2-naphthalenecarboxylic Acid Derivatives of Formula (A)

To a stirred solution of compound of formula (B) (1 mmol) in DMF (10 mL), CuCN (3 mmol) was added and refluxed under $N_2$ atmosphere for 16 h (monitored by TLC). The reaction mixture was cooled to room temperature (20 to 40° C.), then diluted with water (10 mL) and EtOAc (15 mL). The organic layer was separated and the aqueous layer was extracted with EtOAc (2×20 mL). The combined organic extracts were washed with brine and dried over anhyd. $Na_2SO_4$ and concentrated under reduced pressure to give crude products which was purified by column chromatography [silica gel (230-400 mesh) and petroleum ether: EtOAc (70:30) as an eluent] gave 1-Amino-2-naphthalenecarboxylic acid derivatives in 86% yield.

The product, 1-Amino-2-naphthalenecarboxylic acid derivatives compound of formula (A) is characterized and compared with compound of formula (B) by IR, $^1$H NMR, $^{13}$C NMR and elemental analysis. As shown below:

Example 2

Characterization of Ethyl 4-(2-bromo-4,5-dimethoxyphenyl)but-2-enoate

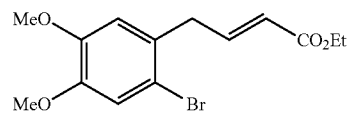 [SMILES: CCOC(=O)/C=C/Cc1cc(OC)c(OC)cc1Br]

Yield: 86%, IR (CHCl$_3$): 765, 784, 1031, 1184, 1318, 1447, 1480, 1594, 1640, 1712, 2225, 2938, 2983 cm$^{-1}$; $^1$H NMR (200 MHz, CDCl$_3$): δ1.28 (t, J=7.22 Hz, 3H), 3.57 (dd, J=1.75, 6.48 Hz, 2H), 3.85 (s, 3H), 3.86 (s, 3H), 4.18 (q, J=7.22 Hz, 2H), 5.74 (dt, J=1.75, 15.52 Hz, 1H), 6.66 (s, 1H), 6.96-7.10 (m, 2H); $^{13}$C NMR (CDCl$_3$): δ14.10, 38.07, 55.81, 55.89, 60.01, 113.03, 114.19, 115.47, 122.37, 128.85, 145.50, 148.39, 165.98; Analysis: $C_{14}H_{17}BrO_4$ requires C 51.08, H 5.21 found C 50.96, H 5.17%.

Example 3

Characterization of ethyl 1-amino-6,7-dimethoxynaphthalene-2-carboxylate

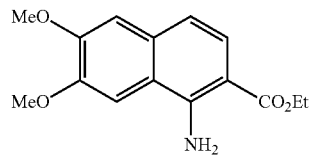 [SMILES: CCOC(=O)c1ccc2cc(OC)c(OC)cc2c1N]

Yield: 85%, IR (CHCl$_3$): 756, 792, 1013, 1181, 1325, 1474, 1480, 1549, 1640, 2983, 2398, 2420 cm$^{-1}$; $^1$H NMR (200 MHz, CDCl$_3$): δ1.42 (t, J=7.10 Hz, 3H), 4.00 (s, 3H), 4.01 (s, 3H), 4.36 (q, J=7.10 Hz, 2H), 6.32 (brs, 1H), 6.94 (d, J=8.86 Hz, 1H), 7.02 (s, 1H), 7.08 (s, 1H), 7.78 (d, J =8.86 Hz, 1H); $^{13}$C NMR (CDCl$_3$): δ 14.36, 55.59, 55.69, 59.97, 101.18, 103.83, 107.09, 114.84, 117.66, 125.18, 132.45, 147.64, 148.60, 150.92, 168.84; Analysis: $C_{15}H_{17}NO_4$ requires C 65.44, H 6.22, N 5.09 found C 65.38, H 6.16, N 4.97%.

Example 4

Ethyl 1-aminonaphthalene-2-carboxylate

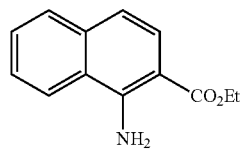

Yield: 85%; gum; IR (CHCl$_3$, cm$^{-1}$): $u_{max}$ 798, 865, 964, 1015, 1135, 1157, 1232, 1264, 1471, 1665, 2965, 3335, 3346; $^1$H NMR (200 MHz, CDCl$_3$): δ1.42 (t, J=7.1 Hz, 3H), 4.36 (q, J=7.1 Hz, 2H), 7.05 (d, J=8.9 Hz, 1H), 7.40-7.56 (m, 2H), 7.72 (d, J=7.8 Hz, 1H), 7.87 (d, J=8.9 Hz, 2H); $^{13}$C-NMR (50 MHz, CDCl$_3$): δ 14.4, 60.1, 104.2, 115.7, 121.4, 123.1, 125.0, 126.6, 128.2, 128.4, 136.4, 148.8, 168.8; Analysis: C$_{13}$H$_{13}$NO$_2$ requires C, 72.54; H, 6.09; N, 6.51; found: C, 73.08; H, 6.34; N, 6.67%.

Example 5

Ethyl 1-amino-6-methoxynaphthalene-2-carboxylate

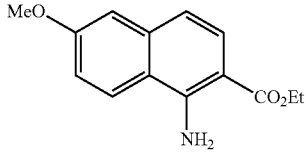

Yield: 78%; gum; IR (CHCl$_3$, cm$^{-1}$): u$_{max}$ 870, 1076, 1245, 1340, 1599, 1672, 3346, 3457; $^1$H NMR (200 MHz, CDCl$_3$): δ 1.41 (t, 3H, J=7.0 Hz), 4.35 (q, J=7.0 Hz, 2H), 6.05 (s, 2H), 6.90 (d, J=8.8 Hz, 1H), 7.00 (s, 1H), 7.16 (s, 1H), 7.75 (d, J=9.0 Hz, 1H); $^{13}$C-NMR (50 MHz, CDCl$_3$): δ 14.5, 55.2, 60.0, 103.1, 107.0, 115.0, 118.0, 123.2, 127.5, 138.3, 148.9, 159.5, 168.8; HRMS (ESI+, m/z): calcd for (C$_{14}$H$_{15}$NO$_3$)$^+$ [(M+Na)$^+$]268.0944; found: 268.0938; Analysis: C$_{14}$H$_{15}$NO$_3$ requires C, 68.56; H, 6.16; N, 5.71; found: C, 68.18; H, 5.99; N, 5.45%.

Example 6

Ethyl 1-amino-6,7-dimethoxynaphthalene-2-carboxylate

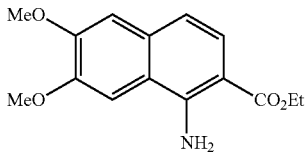 [SMILES: CCOC(=O)c1ccc2cc(OC)c(OC)cc2c1N]

Yield: 74%; Colorless oil; IR (CHCl$_3$, cm$^{-1}$): u$_{max}$ 798, 865, 964, 1015, 1135, 1157, 1232, 1264, 1471, 1665, 2965, 3335, 3346; $^1$H NMR (200 MHz, CDCl$_3$): δ 1.42 (t, J=7.1 Hz, 3H), 4.36 (q, 2H, J=7.1 Hz), 7.05 (d, J=8.9 Hz, 1H), 7.40-7.56 (m, 2H), 7.72 (d, J=7.8 Hz, 1H), 7.87 (d, J=8.9 Hz, 2H); $^{13}$C-NMR (50 MHz, CDCl$_3$): δ 14.4, 60.1, 104.2, 115.7, 121.4, 123.1, 125.0, 126.6, 128.2, 128.4, 136.4, 148.8, 168.8; Analysis: C$_{15}$H$_{17}$NO$_4$ requires C, 65.44; H, 6.22; N, 5.09 found: C, 65.69; H, 6.18; N, 5.11%.

Example 7

Ethyl 1-amino-7,8-dimethoxynaphthalene-2-carboxylate

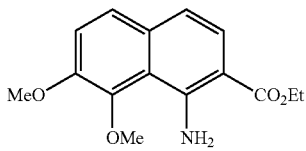

Yield: 73%; Colorless oil; IR (CHCl$_3$, cm$^{-1}$): u$_{max}$ 779, 826, 956, 1018, 1267, 1579, 1672, 3334, 3464; $^1$H NMR (200 MHz, CDCl$_3$): δ 1.41 (t, J=7.2 Hz, 3H), 3.97 (s, 6H), 4.35 (q, J=7.2 Hz, 2H), 6.82 (d, J=10.4 Hz, 1H), 7.24-7.28 (m, 1H), 7.41 (d, J=9.0 Hz, 1H), 7.69 (d, J=9.0 Hz, 1H); $^{13}$C-NMR (50 MHz, CDCl$_3$): δ 14.2, 56.6, 59.6, 61.2, 102.5, 113.8, 116.6, 117.8, 124.2, 125.1, 132.9, 146.8, 148.4, 150.9, 168.6; Analysis: C$_{15}$H$_{17}$NO$_4$ requires C, 65.44; H, 6.22; N, 5.09 found: C, 65.34; H, 6.31; N, 5.12%.

Example 8

Ethyl 1-amino-6-(benzyloxy)-7-methoxynaphthalene-2-carboxylate

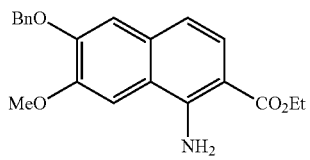 [SMILES: CCOC(=O)c1ccc2cc(OCc3ccccc3)c(OC)cc2c1N]

Yield: 76%; Colorless solid; mp: 144-145° C.; IR (CHCl$_3$, cm$^{-1}$): u$_{max}$ 1247, 1483, 1619, 1676, 3434, 3452; $^1$H NMR (200 MHz, CDCl$_3$): δ 1.41 (t, J=7.1 Hz, 3H), 4.00 (s, 3H), 4.35 (q, 2H, J=7.1 Hz), 5.26 (s, 2H), 6.95 (d, J=8.8 Hz, 1H), 7.04 (s, 1H), 7.18 (s, 1H), 7.30-7.51 (m, 6H), 7.76 (d, J=8.8 Hz, 1H); $^{13}$C-NMR (50 MHz, CDCl$_3$): δ 14.5, 55.8, 60.1, 71.3, 104.3, 107.6, 115.2, 117.9, 125.5, 127.4, 128.1, 128.7, 132.9, 1136.7, 147.5, 147.9, 151.8, 168.9; Analysis: C$_{21}$H$_{21}$NO$_4$ requires C, 71.68; H, 6.02; N, 3.99; found: C, 71.63; H, 5.95; N, 3.89%.

Example 9

Ethyl 1-amino-6-methylnaphthalene-2-carboxylate

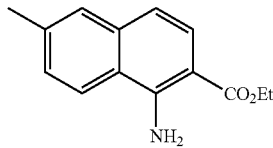 [SMILES: CCOC(=O)c1ccc2cc(C)ccc2c1N]

Yield: 81%; Colorless oil; IR (CHCl$_3$, cm$^{-1}$): u$_{max}$ 1078, 1222, 1239, 1257 1605, 1663, 3352, 3453; $^1$H NMR (200 MHz, CDCl$_3$): δ 1.42 (t, J=7.1 Hz, 3H), 2.55 (s, 3H), 4.37 (q, J=7.1 Hz, 2H), 7.02 (d, J=8.8 Hz, 1H), 7.37 (d, J=8.2 Hz, 1H), 7.63 (d, J=8.1 Hz, 2H), 7.81 (d, J=8.8 Hz, 1H); $^{13}$C-NMR (50 MHz, CDCl$_3$): δ 14.5, 22.0, 60.2, 104.9, 116.1, 120.9, 123.4, 125.7, 128.4, 130.4, 134.6, 134.9, 147.9, 168.9; HRMS (ESI+, m/z): calcd for (C$_{14}$H$_{15}$NO$_2$)$^+$ [(M+Na)$^+$] 252.0995; found: 252.0989; Analysis: C$_{14}$H$_{15}$NO$_2$ requires C, 73.34; H, 6.59; N, 6.11; found: C, 73.26; H, 6.52; N, 6.01%.

Example 10

Ethyl 1-amino-6-fluoronaphthalene-2-carboxylate

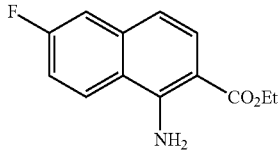 [SMILES: CCOC(=O)c1ccc2cc(F)ccc2c1N]

Yield: 88%; gum; IR (CHCl$_3$, cm$^{-1}$): u$_{max}$ 767, 1249, 1604, 1673, 2987, 3347, 3447; $^1$H NMR (200 MHz, CDCl$_3$): δ 1.43 (t, J=7.1 Hz, 3H), 4.37 (q, J=7.2 Hz, 2H), 6.98 (d, J=8.9 Hz, 1H), 7.15-7.24 (m, 1H), 7.34 (dd, J=2.5, 7.1 Hz, 1H), 7.84-7.92 (m, 2H); $^{13}$C-NMR (50 MHz, CDCl$_3$): δ 14.5, 62.3, 104.1, 111.9, 114.9, 120.0, 124.3, 128.1, 138.1, 148.8, 161.1, 163.6, 168.7; HRMS (ESI+, m/z): calcd for (C$_{13}$H$_{12}$FNO$_2$)$^+$ [(M+Na)$^+$] 256.0744; found: 256.0730; Analysis: C$_{13}$H$_{12}$FNO$_2$ requires C, 66.94; H, 5.19; N, 6.01; found: C, 67.03; H, 5.13; N, 5.89%.

Example 11

Ethyl 1-amino-6-nitronaphthalene-2-carboxylate

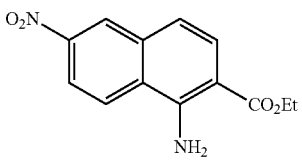 [SMILES: CCOC(=O)c1ccc2cc([N+](=O)[O-])ccc2c1N]

Yield: 91%; Red solid; mp: 176-177° C.; IR (CHCl$_3$, cm$^{-1}$): u$_{max}$ 1243, 1345, 1602, 1674, 3352, 3446; $^1$H NMR (200 MHz, CDCl$_3$): δ 1.45 (t, J=7.0 Hz, 3H), 4.41 (q, J =7.0 Hz, 2H), 6.90 (s, 2H), 7.23 (d, J=8.8 Hz, 1H), 8.02 (t, J=8.8 Hz, 1H), 8.18 (d, J=2.26 Hz, 1H), 8.20 (d, J=2.26 Hz, 1H), 8.64 (d, J=2.0 Hz, 1H); $^{13}$C-NMR (50 MHz, CDCl$_3$): δ 14.4, 60.7, 107.1, 116.8, 118.2, 123.4, 124.4, 125.6, 129.0, 135.6, 147.0, 148.2, 168.2; HRMS (ESI+, m/z): calcd for (C$_{13}$H$_{12}$N$_2$O$_4$)$^+$ [(M+Na)$^+$] 283.0689; found: 283.0682; Analysis: C$_{13}$H$_{12}$N$_2$O$_4$ requires C, 60.00; H, 4.65; N, 10.76; found: C, 59.95; H, 4.51; N, 10.65%.

Example 12

Ethyl 5-aminonaphtho[2,3-d][1,3]dioxole-6-carboxylate

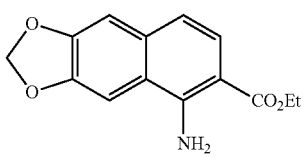 [SMILES: CCOC(=O)c1ccc2cc3c(cc2c1N)OCO3]

Yield: 82%; gum; IR (CHCl$_3$, cm$^{-1}$): u$_{max}$ 1243, 1345, 1602, 1674, 3352, 3446; $^1$H NMR (200 MHz, CDCl$_3$): δ 1.42 (t, J=7.1 Hz, 3H), 3.92 (s, 3H), 4.36 (q, J=7.1 Hz, 2H), 6.97 (d, J=8.8 Hz, 1H), 7.02-7.11 (m, 2H), 7.82 (t, J=8.8 Hz, 2H); $^{13}$C-NMR (50 MHz, CDCl$_3$): δ 14.4, 60.0, 98.7, 101.3, 104.5, 104.9, 115.6, 119.0, 125.5, 134.0, 147.4, 147.8, 149.2, 168.8; Analysis: C$_{13}$H$_{12}$N$_2$O$_4$ requires C, 64.86; H, 5.05; N, 5.40; found: C, 64.79; H, 5.12; N, 5.46%.

Example 13

Ethyl 1-amino-6,7-dimethoxy-5-methylnaphthalene-2-carboxylate

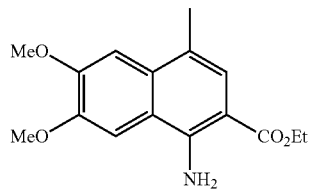 [SMILES: CCOC(=O)c1cc(C)c2cc(OC)c(OC)cc2c1N]

Yield: 81%; Yellow solid; mp: 135-136° C.; IR (CHCl$_3$, cm$^{-1}$): u$_{max}$ 798, 865, 964, 1063, 1205, 1232, 1250, 1462, 1482, 1513, 1602, 1674, 2980, 3352, 3471; $^1$H NMR (200 MHz, CDCl$_3$): δ 1.40 (t, J=7.07 Hz, 3H), 2.50 (s, 3H), 4.02 (s, 6H), 4.32 (q, 2H, J=7.07 Hz), 7.11 (s, 1H), 7.13 (s, 1H), 7.62 (s, 1H); $^{13}$C-NMR (50 MHz, CDCl$_3$): δ 14.3, 18.9, 55.3, 55.4, 59.8, 101.7, 103.5, 103.6, 118.1, 120.1, 131.5, 146.3, 148.0, 150.5, 168.7; Analysis: C$_{16}$H$_{19}$NO$_4$ requires C, 66.42; H, 6.62; N, 4.84; found: C, 66.42; H, 6.38; N, 4.48%.

Example 14

Ethyl 1-aminophenanthrene-2-carboxylate

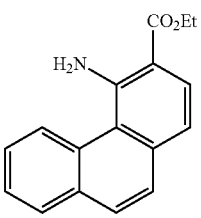 [SMILES: CCOC(=O)c1ccc2ccc3ccccc3c2c1N]

Yield: 71%; Yellow oil; IR (CHCl$_3$, cm$^{-1}$): u$_{max}$ 791, 845, 964, 1052, 1215, 1239, 1240, 1412, 1472, 1533, 1664, 2970, 3332, 3451; $^1$H NMR (200 MHz, CDCl$_3$): δ 1.41 (t, J=7.07 Hz, 3H), 4.34 (q, 2H, J=7.07 Hz), 7.09 (d, J=8.59 , 1H), 7.49-7.64 (m, 1H), 7.70-7.75 (d, J=8.71 Hz, 1H), 7.86 (d, J=8.96 1H), 8.03 (d, J=8.47 1H), 9.17 (d, J=8.21 1H); $^{13}$C-NMR (50 MHz, CDCl$_3$): δ 14.4, 16.4, 108.2, 116.7, 119.1, 124.5, 125.6, 126.5, 127.0, 128.3, 129.1, 129.6, 130.8, 132.8, 137.1, 151.0, 169.1; Analysis: C$_{17}$H$_{15}$NO$_2$ requires C, 76.96; H, 5.70; N, 5.28; found: requires C, 76.71; H, 5.51; N, 5.22

Advantages of the Invention

1. One pot process with good yields obtained
2. Avoids hazardous chemicals

The invention claimed is:

1. A one pot process for the preparation of compound of formula (A) comprising reacting compound of formula (B) with CuCN in DMF at a temperature in the range of 145°-155° C. for period in the range of 10 to 12 hours;

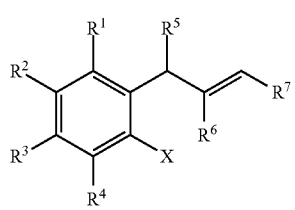

Formula (B)

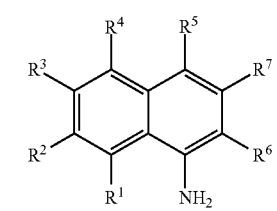

Formula (A)

Wherein, $R^1$, $R^2$, $R^3$, $R^4$ are selected independently from the group consisting of hydrogen, alkyl, alkoxy, halo, $NO_2$ or CN;
$R^5$ is selected independently from the group consisting of H, $CH_3$, $C_2H_5$, Ph or $CH_3C_6H_4$;
$R^6$ is selected independently from the group consisting of $CO_2Et$, $CO_2Me$, $CO_2Ph$, COMe, COPh, CN, $SO_2Ph$, $CONH_2$ or $NO_2$;
$R^7$ is selected independently from the group consisting of H, $CH_3$ or Ph; and
X represents halo group.

2. The process according to claim 1, wherein the halo group is bromo.

3. The process according to claim 1, wherein yield of the compound of formula A ranges between 75 to 90%.

4. The process according to claim 1, wherein the compound of formula (A) is selected from the group consisting of:
Ethyl 1-aminonaphthalene-2-carboxylate;
Ethyl 1-amino-6-methoxynaphthalene-2-carboxylate;
Ethyl 1-amino-6,7-dimethoxynaphthalene-2-carboxylate;
Ethyl 1-amino-7,8-dimethoxynaphthalene-2-carboxylate;
Ethyl 1-amino-6-(benzyloxy)-7-methoxynaphthalene-2-carboxylate;
Ethyl 1-amino-6-methylnaphthalene-2-carboxylate;
Ethyl 1-amino-6-fluoronaphthalene-2-carboxylate;
Ethyl 1-amino-6-nitronaphthalene-2-carboxylate;
Ethyl 5-aminonaphtho[2,3-d][1,3]dioxole-6-carboxylate;
Ethyl 1-amino-6,7-dimethoxy-5-methylnaphthalene-2-carboxylate; and;
Ethyl 1-aminophenanthrene-2-carboxylate.

5. The process according to claim 1, wherein the compound of formula (B) is selected from the group consisting of ethyl 4-(2-halo-4,5-dimethoxyphenyl)but-2-enoate, 1-(2-bromo-3,4,5,6-substituted phenyl)but-2-ene and compounds of formula (B) where:
$R^1$ is H, Ph, $CH_3$, $C_2H_5$ or $CH_3C_6H_4$;
$R^2$ is $CO_2Et$, $CO_2Me$, $CO_2Ph$, COMe, COPh, $SO_2Ph$, $NO_2$, $CONH_2$, CN or $NO_2$, and
$R^3$ is H, $CH_3$ or Ph.

6. Ethyl 1-aminophenanthrene-2-carboxylate.

* * * * *